US007608608B2

(12) United States Patent
Gyurik

(10) Patent No.: US 7,608,608 B2
(45) Date of Patent: *Oct. 27, 2009

(54) PHARMACEUTICAL COMPOSITION

(75) Inventor: Robert J. Gyurik, Exeter, NH (US)

(73) Assignee: CPEX Pharmaceuticals, Inc., Exeter, NH (US)

(*) Notice: Subject to any disclaimer, the term of this patent is extended or adjusted under 35 U.S.C. 154(b) by 0 days.

This patent is subject to a terminal disclaimer.

(21) Appl. No.: 12/359,162

(22) Filed: Jan. 23, 2009

(65) Prior Publication Data

US 2009/0118251 A1    May 7, 2009

Related U.S. Application Data

(63) Continuation of application No. 11/931,809, filed on Oct. 31, 2007, which is a continuation of application No. 10/473,724, filed as application No. PCT/US03/12235 on Apr. 21, 2003, now Pat. No. 7,320,968.

(60) Provisional application No. 60/374,103, filed on Apr. 19, 2002.

(51) Int. Cl.
*A01N 45/00* (2006.01)

(52) U.S. Cl. .................................................. 514/169

(58) Field of Classification Search .................. None
See application file for complete search history.

(56) References Cited

U.S. PATENT DOCUMENTS

| 5,019,395 | A | 5/1991 | Mahjour et al. |
|---|---|---|---|
| 5,023,252 | A | 6/1991 | Hseih |
| 5,855,905 | A | 1/1999 | Oettel et al. |
| 5,968,919 | A | 10/1999 | Samour et al. |
| 6,238,284 | B1 | 5/2001 | Dittgen et al. |
| 6,503,894 | B1 | 1/2003 | Dudley et al. |
| 6,743,448 | B2 | 6/2004 | Krgyer |
| 2002/0058650 | A1 | 5/2002 | Mak et al. |
| 2003/0027804 | A1 | 2/2003 | van der Hoop |
| 2008/0103120 | A1 | 5/2008 | Gyurik |
| 2008/0108590 | A1 | 5/2008 | Gyurik |
| 2008/0275012 | A1 | 11/2008 | Gyurik |

OTHER PUBLICATIONS

Wang, C., et al., Pharmacokinetics of Transdermal Testosterone Gel in Hypgonadal Men: Application of Gel at One Site Versus Four Sites: A General Clinical Research Center Study, The Journal of Clinical Endocrinology & Metabolism, 2000, pp. 964-969, vol. 85, No. 3.

Wang C., et al., Transdermal Testosterone Gel Improves Sexual Function, Mood, Muscle Strength, and Body Composition Parameters in Hypogonadal Men, The Journal of Clinical Endocrinology & Metabolism, 2000, pp. 2839-2853, vol. 85, No. 8.

Cutter, C., Compound Percutaneous Testosterone Gel: Use and Effects in Hypogonadal Men, The Journal of American Board Family Practice, Jan.-Feb. 2001, pp. 22-32, vol. 14, No. 1.

Docket for litigation of parent application U.S. Patent No. 7,320,968 (docket retrieved on May 20, 2009).

Complaint for Patent Infringement filed on Dec. 4, 2008 for litigation of parent application U.S. Patent No. 7,320,968.

*Primary Examiner*—Frederick Krass
*Assistant Examiner*—Benjamin Packard
(74) *Attorney, Agent, or Firm*—Michael A. Davitz

(57) ABSTRACT

A pharmaceutical composition comprising: (A) an androgen; (B) a cyclic enhancer of the type used in the compositions and methods claimed by U.S. Pat. No. 5,023,252 to Hsieh; and (C) a thickening agent; including, for example, a composition in which the cyclic enhancer is a macrocyclic ester or a macrocyclic ketone; the use of the composition to treat a condition, for example, male hypogonadism, in a patient by applying the composition to the membrane of the patient; and a method for making the composition.

8 Claims, 3 Drawing Sheets

Figure 1:
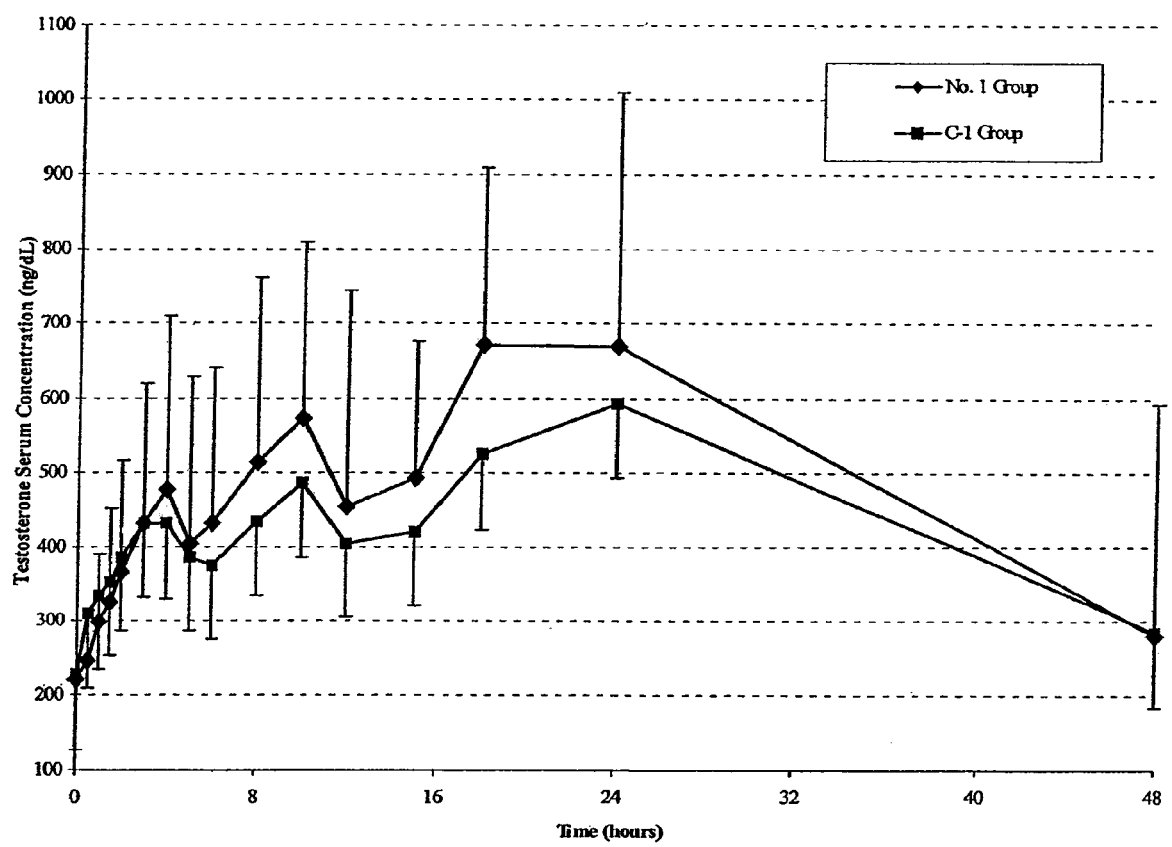

Mean (SD) Total Testosterone (T) Levels Following A Single Dose of No. 1 Group or C-1 Group Testosterone Gel 50 mg TD in 29 Hypogonadal Men Mean (SD) Total Testosterone (T) Levels Following A Single Dose of
No. 1 Group or C-1 Group Testosterone Gel 50 mg TD in 29 Hypogonadal Men Body Composition: Mean Change from Baseline to Day 90

Skin Irritation: Distribution of Subjects with Positive Application Site Irritation Scores

PHARMACEUTICAL COMPOSITION

FIELD OF THE INVENTION

The present invention relates to a composition useful for the delivery of an androgen. More particularly, the present invention relates to a pharmaceutical composition comprising an androgen and an enhancer, that is, a material which is capable of increasing the rate of passage of an androgen through a body membrane.

Androgens include, for example, 17β-hydroxyandrost-4-en-3-one, commonly known as testosterone, and dihydrotestosterone (DHT), a metabolite of testosterone. Testosterone is a naturally-occurring androgen which is secreted in males and, to a much lesser extent, in females. In males, testosterone and DHT are responsible for normal growth and development of the male sex organs and for maintenance of secondary sex characteristics. In females, testosterone and DHT are believed to be important for normal growth, sexual desire, and sexual function. In addition, androgens promote retention of nitrogen, sodium, potassium, and phosphorus, and decrease the urinary excretion of calcium. Androgens have been reported to also increase protein anabolism, decrease protein catabolism, and stimulate the production of red blood cells.

In the blood serum, testosterone exists primarily bound to a protein, typically albumin or sex hormone binding protein. Unbound testosterone is referred to as "free testosterone" (FT). The term "total testosterone" (T) refers to the total amount of testosterone in the blood serum, that is, the combined amount of protein-bound testosterone and free testosterone. The typical half-life of testosterone in the blood serum ranges from 10 to 100 minutes.

Androgens such as testosterone and DHT bind to androgen receptors on cells. The resulting androgen-receptor complex regulates gonadotropin secretion and spermatogenesis. The androgen-receptor complex is responsible also for external virilization and for most androgen actions during sexual maturation and adult life. DHT is an especially potent androgen because it binds with greater affinity to androgen receptors than testosterone does.

Testosterone production is stimulated by luteinizing hormone (LH). It is believed that follicle stimulating hormone (FSH) stimulates testosterone production also. Testosterone concentrations in the blood serum are regulated in part by a negative-feedback pathway in which testosterone inhibits the formation and/or secretion of luteinizing hormone-releasing hormone (LHRH). LHRH stimulates the secretion of LH by the pituitary gland. Testosterone acts also by regulating the sensitivity of the pituitary gland to LHRH.

Male hypogonadism is a disorder in males resulting from or characterized by abnormally-decreased functional activity of the gonads. Male hypogonadism is manifested in the form of below-normal concentration of testosterone in the blood serum. The U.S. Federal Food and Drug Administration estimates that about 4 to 5 million Americans suffer from male hypogonadism and that male hypogonadism affects about 5 in every 1,000 men. It is believed that male hypogonadism affects 1 out of every 5 men aged over 50. Primary male hypogonadism is caused by testicular failure. Secondary male hypogonadism is caused by idiopathic gonadotropin, LHRH deficiency, or pituitary-hypothalamic injury. Various other causes of male hypogonadism include, for example, decline in the number of Leydig cells in the testes due to old age, and primary organic causes. Symptoms associated with male hypogonadism include decreased sexual desire with or without impotence, depression, decreased libido, fatigue and loss of energy, erectile dysfunction, mood depression, osteoporosis, reduced lean body mass, decreased muscle mass, decreased bone density, and regression of secondary sex characteristics.

Females with below-average androgen concentration in the blood serum suffer also from disorders related to androgen deficiency. Causes of androgen deficiency in females include aging, oophorectomy, and ovary failure. Symptoms associated with female androgen deficiency include female sexual dysfunction, lack of desire, and muscle wasting.

Normal concentration of androgen in the blood serum may be achieved in patients with the administration of exogenous androgen. It has been well documented that administration of exogenous androgen results in the maintenance or restoration of male secondary sexual characteristics, sexual behavior, energy, mood, and muscle development as well as a decrease in the percentage of fat in body composition and an improvement in bone density.

Various methods for administering exogenous androgen have been developed. Optimally, such methods should not only raise the concentration of androgen in the blood serum but also, because of the short half-life of androgen, allow for normalization of androgen delivery into the blood serum over an extended period of time, thus maintaining an effective concentration of androgen in the blood serum over an appropriate period of time and avoiding undesirable effects which may result from sudden increases and declines in androgen concentration in the blood serum. In addition, such methods preferably result in minimal or no adverse effects, such as irritation, damage to the body, and pain.

The oral delivery of exogenous androgen has been used to treat hypogonadism. Androgen delivered orally, however, is first absorbed from the gastrointestinal tract. Such absorption is irregular and thus often results in sudden increases and declines in androgen concentration in the blood serum. Furthermore, androgen which is absorbed through the gastrointestinal tract passes into the portal circulation and is degraded rapidly by the liver. Only a relatively small amount of androgen enters the systemic circulation. The passage of androgen through the portal circulation system and the liver may also result in adverse effects.

Exogenous androgen may alternatively be delivered parenterally directly into the systemic circulation. Such delivery allows for androgen to enter the systemic circulation directly, avoiding the gastrointestinal tract and the liver. Androgen delivered parenterally, however, is absorbed rapidly from the injection vehicle into the blood serum thus making a sustained delivery of androgen difficult to achieve and resulting in a sudden increase in androgen concentrations in the blood serum followed by a gradual decline. The rate of androgen absorption can be retarded with the use of esterified forms of androgen. Esterified forms of androgen are more soluble than non-esterified forms of androgen in the lipidic vehicles typically used for parenteral delivery. Such esterified forms of androgen, however, are rapidly de-esterified in the blood serum and thus sustained delivery of androgen remains difficult to maintain. In addition, the absorption of androgen from the injection vehicle is irregular, thus leading to sudden fluctuations in androgen concentration in the blood serum. Furthermore, parenteral delivery is uncomfortable and leads to problems of patient compliance.

The transdermal delivery of androgen avoids many of the disadvantages of oral and parenteral delivery. Such delivery is relatively painless and allows androgen to enter systemic circulation without having to first pass through the gastrointestinal tract or the liver.

One method for transdermal delivery of androgen involves the use of a transdermal patch which is adhered to the surface of the skin of the patient and which contains a reservoir of androgen that is absorbed by the skin. Such patches, however, cause irritation of the skin, are often painful to remove, and are dislodged easily. Moreover, such patches are indiscrete in that they are noticeable when not covered, are large and bulky, and may leave a discolored area of skin after removal. In addition, the compositions contained in such patches are also often irritating to the skin.

Another method for transdermal delivery of androgen involves the application directly to the skin of an androgen-containing composition in the form of a gel. Such a gel is referred to herein as a "topical gel" to distinguish it from other compositions which are in a gel form and which are contained within an article that is applied to the skin, for example, a transdermal patch.

The present invention relates to the provision of an improved androgen-containing composition which can be applied directly to the skin for sustained delivery of androgen to an individual in need thereof.

Reported Developments

There have been developed androgen-containing compositions in the form of a topical gel applied directly to the skin, for example, to the back, shoulders, upper arms, abdomen, or thighs. The use of such topical gels overcomes the previously-mentioned negative effects of a patch as well as the previously-mentioned negative pharmacokinetic effects of oral and parenteral androgen administration. In addition, since such a topical gel is typically in contact with a larger area of the skin relative to that contacted by a patch and, since the skin serves as an appropriate reservoir for the androgen delivered, a consistent normalization of androgen delivery into the blood serum over an extended period of time is able to be achieved.

The ability of an androgen gel to deliver androgen effectively is often dependent on whether an enhancer, that is, a material which is capable of increasing the rate of passage of androgen through the skin or other body membrane, is used and the type of enhancer used Examples of topical androgen gels include those described in U.S. Pat. Nos. 5,968,919 to Samour et al. and 6,503,894 to Dudley et al. The '919 patent describes a topical testosterone gel comprising also a dioxolane or a dioxane compound which functions as an enhancer. The topical testosterone gel described in the '894 patent (sold as AndroGel® by Solvay Pharmaceuticals, Inc., Marietta, Ga., U.S.A.) also contains an enhancer, namely, isopropyl myristate.

Disadvantages associated with the aforementioned topical androgen gels include, for example, the inconsistency of the gels and the lack of emollient properties; their use leads to drying of the skin and skin irritation. In addition, the gel of the '894 patent is capable of delivering a relatively low amount of testosterone through the skin and the gel of the '919 patent contains an enhancer which tends to irritate the skin.

SUMMARY OF THE INVENTION

In accordance with this invention, there is provided a pharmaceutical composition comprising: (A) an androgen; (B) a cyclic enhancer of the type described in U.S. Pat. No. 5,023,252 to Hsieh (assigned to the same assignee as that of the present invention); and (C) a thickening agent. In preferred form, such a composition exists in the form of a gel and comprises an enhancer which is a cyclic ester or a cyclic ketone.

Another aspect of the present invention is a unit dose formulation which is effective in supplying testosterone transdermally to the blood of a male patient such that, following a single application of the unit dose to the patient, the amount of circulating testosterone ($AUC_{0-24}$) in the blood serum of the patient achieved in the 24-hour period following the application is about 100 to about 35,000 ng·h/dL greater than the amount of circulating testosterone ($AUC_{0-24}$) in the blood serum of the patient that would have been achieved in the same 24 hour period had the dose not been administered, said unit dose comprising up to about 1% by weight testosterone, about 0.01 to about 25% by weight of a cyclic enhancer of the type described in U.S. Pat. No. 5,023,252 to Hsieh, and about 0.1 to about 10% by weight of thickening agent, said testosterone being present in said unit dose in an amount of about 1 to about 300 mg.

Another aspect of the present invention is a unit dose formulation which is effective in supplying testosterone transdermally to the blood of a female patient such that, following a single application of the unit dose to the patient, the amount of circulating testosterone ($AUC_{0-24}$) in the blood serum of the patient achieved in the 24-hour period following the application is about 0.10 to about 11,700 ng·h/dL greater than the amount of circulating testosterone ($AUC_{0-24}$) in the blood serum of the patient that would have been achieved in the same 24-hour period bad the dose not been administered, said unit dose comprising up to about 1% by weight testosterone, about 0.01 to about 25% by weight of a cyclic enhancer of the type described in U.S. Pat. No. 5,023,252 to Hsieh, and about 0.1 to about 10% by weight of thickening agent, said testosterone being present in said unit dose in an amount of about 0.01 to about 100 mg.

Another aspect of the present invention is a unit dose formulation which is effective in supplying dihydrotestosterone transdermally to the blood of a male patient such that, following a single application of the unit dose to the patient, the amount of circulating dihydrotestosterone ($AUC_{0-24}$) in the blood serum of the patient achieved in the 24-hour period following the application is about 11,625 to about 465,000 pg·h/mL greater than the amount of circulating dihydrotestosterone ($AUC_{0-24}$) in the blood serum of the patient that would have been achieved in the same 24-hour period had the dose not been administered, said unit dose comprising up to about 1% by weight dihydrotestosterone, about 0.01 to about 25% by weight of a cyclic enhancer of the type described in U.S. Pat. No. 5,023,252 to Hsieh, and about 0.1 to about 10% by weight of thickening agent, said dihydrotestosterone being present in said unit dose in an amount of about 5 to about 200 mg.

Another aspect of the present invention is a unit dose formulation which is effective in supplying dihydrotestosterone transdermally to the blood of a female patient such that, following a single application of the unit dose to the patient, the average dihydrotestosterone concentration ($AUC_{0-24}$) in the blood serum of the patient achieved in the 24-hour period following the application is about 11.6 about 232,500 pg·h/mL greater than the average dihydrotestosterone concentration ($AUC_{0-24}$) in the blood serum of the patient that would have been achieved in the same 24-hour period had the dose not been administered, said unit dose comprising up to about 1% by weight dihydrotestosterone, about 0.01 to about 25% by weight of a cyclic enhancer of the type described in U.S. Pat. No. 5,023,252 to Hsieh, and about 0.1 to about 10% by weight of thickening agent, said dihydrotestosterone being present in said unit dose in an amount of about 0.005 to about 100 mg.

Yet another aspect of the present invention is the provision of a method for treating a condition in a patient comprising the step of delivering to said patient a composition comprising an androgen, a cyclic enhancer of the type described in U.S. Pat. No. 5,023,252 to Hsieh, and a thickening agent.

Yet another aspect of the present invention is the provision of a method for treating a condition in a patient comprising the step of applying, once daily, to the shoulder or upper arm of a patient, a unit dose formulation which is effective in supplying testosterone transdermally to the blood of a patient such that, following a single application of the unit dose to the patient, the amount of circulating testosterone ($AUC_{0\text{-}24}$) in the blood serum of the patient achieved in the 24-hour period following the application is about 100 to about 35,000 ng·h/dL greater than the amount of circulating testosterone ($AUC_{0\text{-}24}$) in the blood serum of the patient that would have been achieved in the same 24-hour period had the dose not been administered, said unit dose comprising up to about 1% by weight testosterone, about 0.01 to about 25% by weight of a cyclic enhancer of the type described in U.S. Pat. No. 5,023,252, and about 0.1 to about 1-0% by weight of thickening agent, said testosterone being present in said unit dose in an amount of about 1 to about 300 mg.

Yet another aspect of the present invention is a method for making a composition useful for treating a condition in a patient comprising the step of mixing an androgen, a cyclic enhancer of the type described in U.S. Pat. No. 5,023,252 to Hsieh, and a thickening agent.

DETAILED DESCRIPTION OF DRAWINGS

FIG. 1 is a graph comparing the 48-hour total testosterone pharmacokinetic profile for a first group of hypogonadal men following treatment with a single 5.0 g dose of a composition of the present invention with the 48-hour total testosterone pharmacokinetic profile for a second group of hypogonadal men following treatment with a single 5-0 g dose of the composition described in Comparative Example C-1 below.

Figure 2:
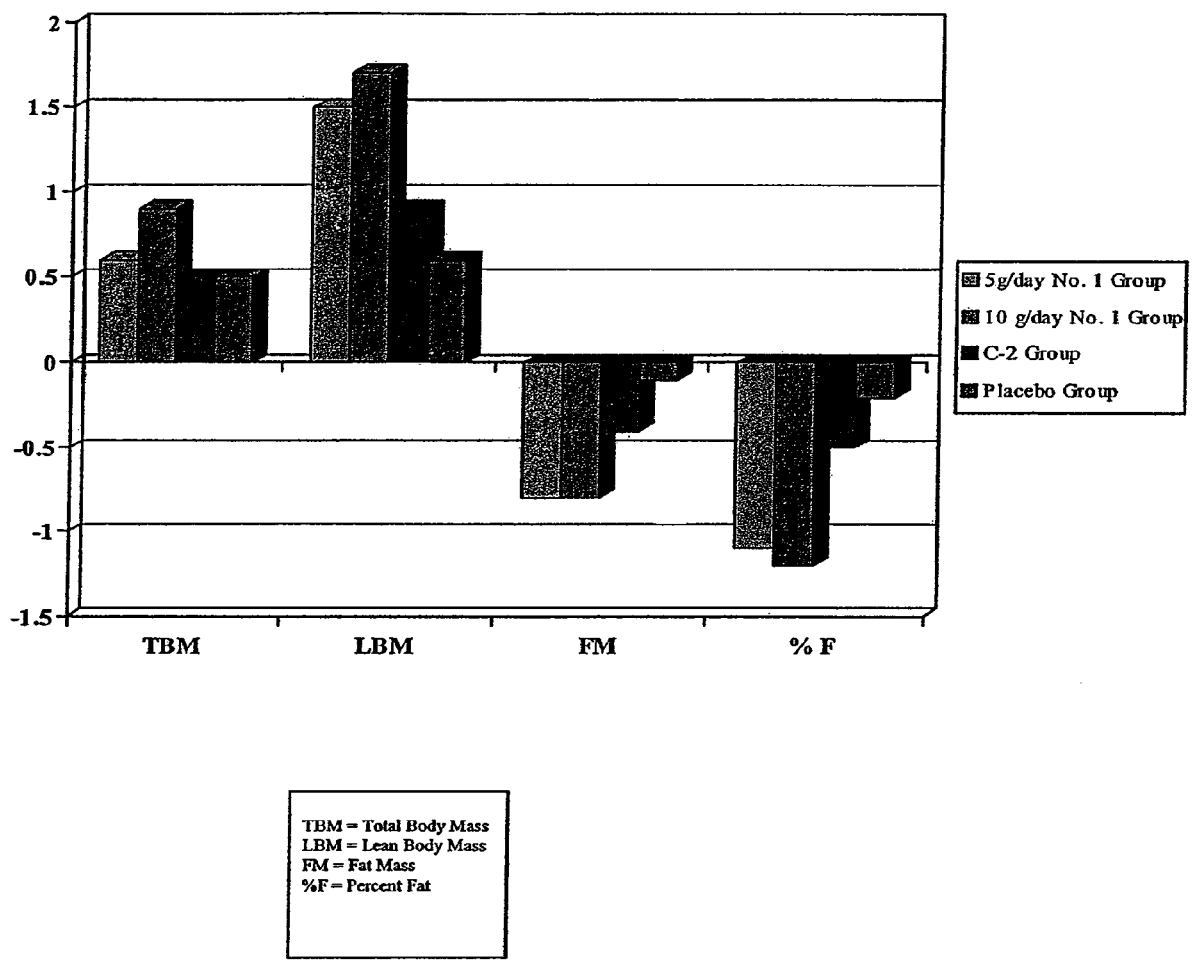

FIG. 2 is a graph comparing the mean change in body composition from baseline to Day 90 for patients treated daily using 5 g/day of a composition of the present invention, patients treated using 10 g/day of this composition, patients treated using 2 patches/day containing the composition described in Comparative Example C-2 below, and patients who applied 10 g/day of a placebo composition.

Figure 3:
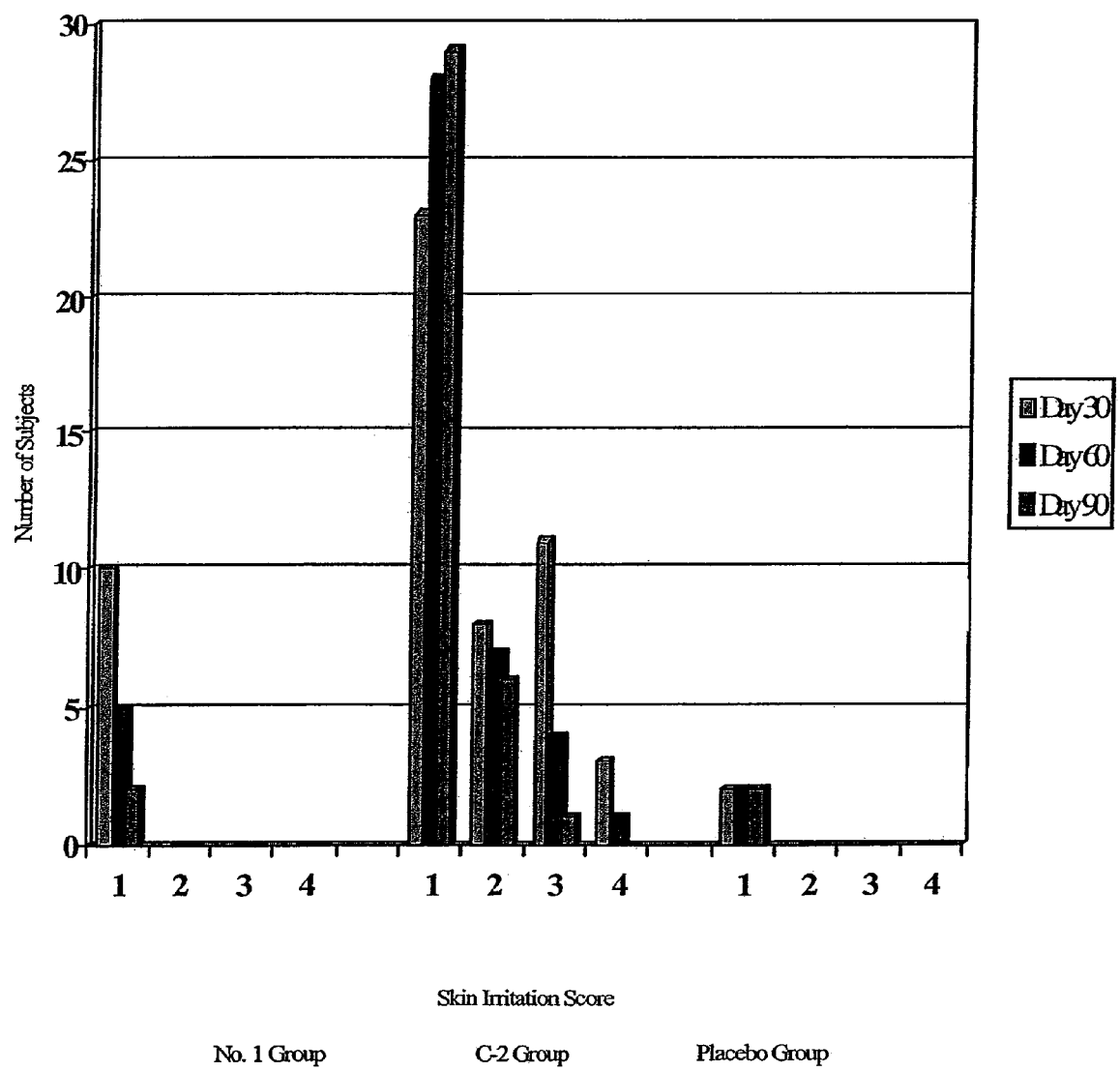

FIG. 3 is a graph comparing skin irritation scores at Days 30, 60, and 90 for patients treated daily using 5 g/day of a composition of the present invention, patients treated using 10 g/day of this composition, patients treated using 2 patches/day containing the composition described in Comparative Example C-2 below, and patients who applied 10 g/day of a placebo composition.

DETAILED DESCRIPTION OF THE INVENTION

The composition of the present invention comprises an androgen. As used herein, the term "androgen" refers to: testosterone; dihydrotestosterone (DHT); and precursors, congeners, salts, complexes, and analogs of testosterone and DHT. Examples of precursors of testosterone and DHT include, for example, DHEA, pregnenolone, progesterone, 17-OH-progesterone, and androsterone. Examples of analogs of testosterone and DHT include: testosterone esters, including straight and branched $C_{1\text{-}8}$ alkyl esters (herein referred to as "simple alkyl esters"), for example, testosterone enanthate, testosterone propionate, testosterone undecanoate, and testosterone heptylate, and cycloaliphatic esters, for example, testosterone cypionate, testosterone cyclopentyl alkyl ester, and testosterone cyclohexyl alkyl ester; and the analogous esters of DHT.

Androgen is present in the composition in a pharmaceutically-effective concentration. For guideline purposes, it is believed most applications will involve the use of the androgen in an amount of about 0.01 to about 15 wt. % of the composition, more likely an amount of about 0.01 to about 10 wt. % of the composition, and most likely in an amount of about 0.1 to about 5 wt. % of the composition.

The composition of the present invention comprises also an enhancer, that is, a compound capable of increasing the rate of passage of an androgen through a body membrane, for example, skin and mucous membranes. The enhancer of the present invention is a compound of the structural formula:

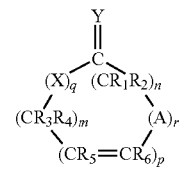

wherein X and Y are oxygen, sulfur or an imino group of the structure

or =N—R; with the proviso that when Y is an imino group, X is an imino group, and when Y is sulfur, X is sulfur or an imino group; A is a group having the structure

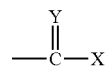

wherein X and Y are as defined above; m and n are integers having a value from 1 to 20 and the sum of m+n is not greater than 25; p is an integer having a value of 0 or 1; q is an integer having a value of 0 or 1; r is an integer having a value of 0 or 1; and each of R, $R_1$, $R_2$, $R_3$, $R_4$, $R_5$, and $R_6$ is independently hydrogen or an alkyl group having from 1 to 6 carbon atoms which may be straight chained or branched, provided that only one of $R_1$ to $R_6$ can be all group; with the proviso that when p, q and r are 0 and Y is oxygen, then m+n is at least 11; and with the further proviso that when X is an imino group, q is equal to 1, Y is oxygen, and p and r are 0, then m+n is at least 11.

Enhancers of the above structural formula are referred to herein as "Hsieh enhancers" and are described, for example, in aforementioned U.S. Pat. No. 5,023,252. Such enhancers are lipophilic and are "membrane-compatible", meaning is that they do not cause damage to the membrane on which the composition of the composition of the present invention is to be applied (hereafter "target membrane"). Such enhancers produce also a low level of irritability or no irritability to the target membrane and, in fact, serve as an emollient.

Preferred Hsieh enhancers for use in the present invention are macrocyclic enhancers. The term "macrocyclic" is used herein to refer to cyclic compounds having at least 12 carbons in the ring. Examples of preferred macrocyclic enhancers for use in the present invention include: (A) macrocyclic ketones, for example, 3-methylcyclopentadecanone (muscone), 9-cycloheptadecen-1-one (civetone), cyclohexadecanone, and cyclopentadecanone (normuscone); and (B) macrocyclic esters, for example, pentadecalactones such as oxacyclohexadecan-2-one (cyclopentadecanolide; ω-pentadecalactone).

Oxacyclohexadecan-2-one and cyclopentadecanone are especially preferred. It has been observed during human clinical testing that only 2 to 4% of patients experienced application site events (e.g., erythema) when a composition of the present invention comprising oxacyclohexadecan-2-one was applied to a target membrane.

The enhancer is present in the composition in a concentration effective to enhance penetration through the membrane of the androgen to be delivered. Various considerations should be taken into account in determining the amount of enhancer to use. Such considerations include, for example, the amount of flux (rate of passage through the membrane) achieved and the stability and compatibility of the components in the formulations. For guideline purposes, it is believed most applications will involve the use of the enhancer in an amount of about 0.01 to about 25 wt. % of the composition, more likely in an amount of about 0.1 to about 15 wt. % of the composition, and most likely in an amount of about 0.5 to about 15 wt. % of the composition.

The composition of the present invention comprises also a thickening agent for use in increasing the viscosity of the composition. Increased viscosity retards the flow of the composition, thus allowing for improved surface cling. Increased viscosity retards also the movement of particles dispersed in the composition, allowing for compounds dispersed therein to remain suspended therein for relatively long periods of time. For guideline purposes, it is believed applications comprising testosterone or its precursors, congeners, salts, complexes, or analogs will involve the use of a gel with a viscosity of about 500 to about 20,000 cps, more likely about 2,000 cps to about 6,000 cps, and most likely about 2,800 cps to about 4,600 cps (as measured under standard conditions of measurement). It is believed applications comprising DHT or its congeners, salts, complexes, or analogs will involve the use of a gel with a viscosity of about 1,000 cps to 9,000 cps, more likely about 2,000 cps to about 8,000 cps and most like about 3,000 cps to about 7,000 cps (as measured under standard conditions of measurement).

Essentially any suitable thickening agent or mixture of thickening agents can be used in the practice of the present invention. Preferred thickening agents are characterized by at least one of the following properties: low level of irritability or no irritability to the target membrane; bioadhesiveness; and being listed in the National Formulary or the U.S. Pharmacopeia. Preferred sources of thickening agents are those which do not include also residual components which may be detrimental to the membrane, for example, benzene and toluene. In addition, preferred thickening agents are those that are synthetic and not obtained from natural sources, thus reducing the risk of unwanted impurities.

As stated above, preferred thickening agents for use in the present invention include those which produce a low level of irritability or no irritability to the target membrane. Examples of such thickening agents include: cellulosic thickening agents, for example, cellulose, hydroxyethyl-cellulose, carboxymethylcellulose, and hydroxypropylmethyl-cellulose; and acrylic thickening agents. Examples of preferred acrylic thickeners are carbomers, for example, non-linear polymers of acrylic acid cross-linked with a polyalkenyl polyether.

Examples of preferred carbomers which may be used in the present invention include carboxypolymethylene, carboxyvinyl polymer, and alkyl acrylates, for example, acrylic acid/alkyl methacrylate copolymer. All of the above are available from Noveon, with carboxypolymethylene sold as Carbopol 980®, carboxyvinyl polymer sold as Carbopol 940®, and acrylic acid/alkyl methacrylate copolymer sold as Pemulen TR-1®. Additional information regarding the above carbomers is provided in Noveon publications TDS-57, 60, 61, 93, 94, 103, 114, 117, 118, 124, 164, 232-3, 237, 244 and TOX-001. In addition, in compositions in which acrylic acid/alkyl methacrylate copolymer (Pemulen TR-1®) is not used as the primary thickening agent, it is preferred that such be present as a co-thickening agent. This is because acrylic acid/alkyl methacrylate copolymer provides the composition with a smoother feel as compared with compositions which do not use acrylic acid/alkyl methacrylate copolymer and serves also as an emollient.

The thickening agent is present in the composition in a concentration effective to provide the desired viscosity to the composition. For guideline purposes, it is believed most applications will involve the use of the thickening agent in an amount of about 0.1 to about 10 wt. % of the composition and more likely in an amount of about 1 to about 6 wt. % of the composition.

The composition of the present invention may comprise also a carrier which is capable of solubilizing one of more of the ingredients comprising the composition of the present invention. Essentially any suitable carrier or mixture of carriers which is a suitable vehicle for the composition of the present invention can be used in the practice thereof. Preferred carriers are characterized by at least one of the following properties: low irritability or no irritability to the target membrane; being listed in the National Formulary or the U.S. Pharmacopeia; capability to enhance penetration of the androgen across a membrane; and capability to perform an additional function in the composition, for example, function also as an emollient, a humectant, a plasticizer, a lubricating agent, and/or a protein stabilizer.

Essentially any solvent capable of solvating at least one of the compounds of the composition of the present invention may be used. Alcohols are preferred primary solvents for use in the present invention because they are capable of solvating the active compounds and the thickening agent and, in compositions in which carbomers are used as the thickening agent, serve to swell the thickening agent. It is believed that alcohols may serve also to enhance the penetration of an androgen across a membrane. Examples of preferred alcohols are lower alkanols, for example, ethanol and isopropanol since such are capable of rapid evaporation, thus ensuring adequate permeation of the androgen though the target membrane.

Preferred co-solvents include glycerin, propylene glycol, polyethylene, polypropylene, and silicones. In addition to serving as co-solvents, glycerin serves as a humectant, an emollient, a plasticizer which plasticizes the stratum corneum of the skin, and a permeation enhancer and propylene glycol serves as an emollient and a permeation enhancer.

The carrier is present in the composition in a concentration effective to serve as a suitable vehicle for the compositions of the present invention. For guideline purposes, it is believed that most applications will involve the use of the carrier in an amount of about 40 to about 98 wt. % of the composition and more likely in an amount of about 50 to about 98 wt. % of the composition.

In preferred form, applications will involve the use of a lower alkanol in an amount of at least about 40 wt. % of the composition and generally about 40 to about 80 wt. % of the composition, more likely in an amount of about 50 to about 75 wt. % of the composition, and most likely in an amount of about 60 to about 75 wt. % of the composition.

In situations where a greater flux for a certain compound is desired, a carrier may be designed in which a first fluid which is miscible with or solvates the compound of interest evaporates more readily than a second fluid, which is immiscible with or partially miscible with or does not solvate the compound of interest. In such situations, when the first fluid evaporates, the compound of interest is left in a supersaturated environment in which it is favorable for the compound to pass into a less saturated environment, in this case through the membrane. For example, oxacyclohexadecan-2-one is miscible with ethanol, but only partially miscible with propylene glycol and immiscible with water. Accordingly, if increased flux for oxacyclohexadecan-2-one is desired, a carrier may include ethanol and propylene glycol and/or water. As another example, testosterone is soluble in ethanol but not soluble in water and partially soluble in propylene glycol. Accordingly, if increased flux for testosterone is desired, a carrier may include ethanol and water or ethanol and propylene glycol. In addition, water may be used to prevent "reverse-flux", or the flow of water from the membrane into the matrix of the composition.

The composition of the present invention may comprise also a crystallization inhibitor capable of inhibiting the crystallization of an androgen. Essentially any suitable crystallization inhibitor or mixture of such inhibitors can be used in the practice of the present invention. Preferred crystallization inhibitors function by lowering the temperature at which an androgen crystallizes. An example of such a crystallization inhibitor is polyethylene glycol 1000.

The crystallization inhibitor is present in the composition in a concentration effective to inhibit the crystallization of the androgen. For guideline purposes, it is believed that most applications which comprise a crystallization inhibitor will involve the use of the crystallization inhibitor in an amount of about 0.001 to about 5 wt. % of the composition, more likely about 0.01 to about 2 wt. % of the composition, and most likely about 0.1 to about 1 wt. % of the composition.

The composition of the present invention may comprise also a preservative capable of preventing oxidation of the components of the composition, microbial growth, or contamination. Essentially any suitable preservative or mixture of preservatives may be used in the practice of the present invention. Preferred preservatives include: food additive antimicrobial agents, for example, quaternary ammonium salts, sorbic acid, acetic acid, and benzoic acid or salts thereof; and antioxidants, for example, Vitamin C, Vitamin E, butylated hydroxyanisole (BHA), and butylated hydroxytoluene (BHT). Examples of preferred antimicrobial preservatives include benzalkonium chloride and cetyl pyridinium chloride.

The preservative is present in the composition in a concentration effective to inhibit microbial growth, the oxidation of the components of the composition, or contamination of the composition. For guideline purposes, it is believed that most applications which comprise a preservative will involve the use of the preservative in an amount of about 0.0001 to about 1.0 wt-% of the composition and more likely in an amount of about 0.005 to about 0.1 wt. % of the composition.

In compositions in which the use of a thickening agent may require neutralization to achieve a desired thickening for the composition, a neutralizing agent may be included in the composition. Carbomers, as acidic molecules, require neutralization, preferably to a pH of between 3 and 9, to achieve their maximum viscosity. Essentially any suitable neutralizing agent or mixture of neutralizing agents can be used in the practice of the present invention. Preferred neutralizing agents are characterized by at least one of the following properties: a pKa greater than about 9, with a pKa greater than about 9.5 being particularly preferred; and being compendial and approved for use by governmental agencies in pharmaceutical formulations. Examples of the neutralizing agents which exhibit both of the above properties include triethanol amine, tromethamine, tris ammo, triethylamine, 2-amino-2-methyl-1-propanol, sodium hydroxide, ammonium hydroxide, and potassium hydroxide.

The choice of neutralizing agent for use in the present application should take into account the thickening agent used. When a solvent is used the choice of neutralizing agent should take into account the primary solvent for the composition and the concentration of the primary solvent in the composition. If an inappropriate neutralizing agent is used, the thickening agent may precipitate out of solution. Noveon publication TRS-237 provides a chart showing examples of appropriate neutralizing agents for compositions with certain concentrations of alcoholic solvent.

The neutralizing agent is present in the composition in a concentration effective to provide the desired viscosity to the composition. For guideline purposes, it is believed that most applications which comprise a neutralizing agent will involve the use of the neutralizing agent in amount which will be sufficient to bring the pH of the composition to between about 3 and about 9, more likely between about 4 and about 8.

The composition of the present invention may include also additional optional ingredients which are art-recognized and in art-recognized quantities. For example, materials may be added to modify the rheology, feel, slip, stability, humectancy, fragrance and other desirable physical properties that a practitioner may deem desirable. In addition, buffers may be added to maintain the composition at a certain pH.

The composition of the present invention may exist in various forms, for example, a gel, a cream, a lotion, an ointment, or a thickened solution. The composition preferably exists in the form of a gel.

In preferred form, the composition exists in the form of a homogeneous gel which is capable of remaining homogeneous over the pharmaceutical lifetime thereof.

The composition of the present invention preferably exhibits good yield value. Yield value measures the resistance of a composition to break down upon stress (e.g., when being rubbed onto skin). The composition should preferably also be capable of allowing for a consistent normalization of androgen delivery into the blood serum over an extended period of time. Additional preferred properties of the composition include emolliency (the producing of a low level of irritability or no irritability to a target membrane), lubricity, and ability to avoid pilling.

The composition of the present invention, when used to deliver testosterone to a male patient, may be delivered in the form of a unit dose formulation which contains testosterone in an amount such that, following a single application of the unit dose to the patient, the amount of circulating testosterone ($AUC_{0-24}$) in the blood serum of the patient achieved in the 24-hour period following the application is about 100 to about 35,000 ng·h/dL, preferably about 600 to about 23,500 ng·h/dL, and most preferably about 2,900 to about 11,700 ng·h/dL greater than the amount of circulating testosterone ($AUC_{0-24}$) in the blood serum of the patient that would have been achieved in the same 24-hour period had the dose not been administered. Such a unit dose for male patients will involve the use of about 1 to about 300 mg of testosterone, more likely an amount of about 5 to about 200 mg testosterone, and most likely in an amount of about 25 to about 100 mg testosterone. In preferred form, the unit dose contains up to about 1 wt. % testosterone.

The composition of the present invention, when used to deliver testosterone to a female patient, may be delivered in the form of a unit dose formulation which contains testosterone in an amount such that, following a single application of the unit dose to the patient, the amount of circulating testosterone ($AUC_{0-24}$) in the blood serum of the patient achieved in the 24-hour period following the application is about 0.10 to about 11,700 ng·h/dL, preferably about 100 to about 8,800 ng·h/dL, and most preferably about 600 to about 6,000 ng·h/dL greater than the average testosterone concentration ($AUC_{0-24}$) in the blood serum of the patient that would have been achieved in the same 24-hour period had the dose not been administered. Such a unit dose for female patients will involve the use of about 0.01 to about 100 mg of testosterone, more likely an amount of about 1 to about 75 mg testosterone, and most likely in an amount of about 5 to about 50 mg testosterone. In preferred form, the unit dose contains up to about 1 wt. % testosterone.

The composition of the present invention, when used to deliver DHT to a male patient, may be delivered in the form of a unit dose formulation which contains DHT in an amount such that, following a single application of the unit dose to the patient, the amount of circulating DHT ($AUC_{0-24}$) in the blood serum of the patient achieved in the 24-hour period following the application is about 11,625 to about 465,000 pg·h/mL, preferably about 23,250 to about 232,500 pg·h/mL, and most preferably about 46,500 to about 116,250 pg·h/mL greater than the amount of circulating DHT ($AUC_{0-24}$) in the blood serum of the patient that would have been achieved in the same 24-hour period had the dose not been administered. Such a unit dose for male patients will involve the use of about 5 to about 200 mg of DHT, more likely an amount of about 10 to about 100 mg DHT, and most likely in an amount of about 20 to about 50 mg DHT. In preferred form, the unit dose contains up to about 1 wt. % DHT.

The composition of the present invention, when used to deliver DHT to a female patient, may be delivered in the form of a unit dose formulation which contains DHT in an amount such that, following a single application of the unit dose to the patient, the amount of circulating DHT ($AUC_{0-24}$) in the blood serum of the patient achieved in the 24-hour period following the application is about 11.6 to about 232,500 pg·h/mL, preferably about 116 to about 116,250 pg·h/mL, and most preferably about 2,325 to about 58,100 pg·h/mL greater than the amount of circulating DHT ($AUC_{0-24}$) in the blood serum of the patient that would have been achieved in the same 24-hour period had the dose not been administered. Such a unit dose for female patients will involve the use of about 0.005 to about 100 mg of DHT, more likely an amount of about 0.05 to about 50 mg DHT, and most likely in an amount of about 1 to about 25 mg DHT. In preferred form, the unit dose contains up to about 1 wt. % DHT.

The composition of the present invention in gel form may be contained in a tube, a sachet, or a metered pump. Such a tube or sachet may contain one unit dose of the composition. A metered pump may be capable of dispensing one metered dose of the composition.

A condition in a patient related to below-normal androgen concentration in the blood serum of the patient may be treated by administering to the patient a composition of the present invention. The composition may be delivered topically. If the composition is in the form of a gel, the composition may be rubbed onto a membrane of the patient, for example, the skin, preferably intact, clean, and dry skin, of the shoulder or upper arm and or the upper torso, and maintained thereon for a period of time sufficient for delivery of androgen to the blood serum of the patient.

The dosage amount will depend upon the condition to be treated, the frequency of administration of the dose, and the amount of androgen in the composition. For the purpose of treating male hypogonadism, a preferred once daily dosage amount of a 1% testosterone gel of the present invention contains about 0.1 to about 30 grams of the composition, more preferably about 0.5 to about 20 grams of the composition, and most preferably about 2.5 to about 10 grams of the composition. A preferred once daily dosage amount of a 1% DHT gel of the present invention for the treatment of male hypogonadism contains about 0.5 to about 20 grams of the composition, more preferably about 1 to about 10 grams of the composition, and most preferably about 2 to about 5 grams of the composition. For purpose of treating female testosterone deficiency, a preferred once daily dosage amount of a 1% testosterone gel of the present invention contains about 0.001 to about 10 grams of the composition, more preferably about 0.1 to about 7.5 grams of the composition, and most preferably about 0.5 to about 5 grams of the composition. A preferred once daily dosage amount of a 1% DHT gel of the present invention for the treatment of female testosterone deficiency contains about 0.0005 to about 10 grams of the composition, more preferably about 0.005 to about 5 grams of the composition, and most preferably about 0.1 to about 2.5 grams of the composition. If, after a period of time has passed following the initial administration of the composition (for example, about 7 to 14 days), the desired clinical response has not been achieved or if the androgen concentration in the blood serum of the patient is determined and found to remain below the normal adult concentration thereof, the amount of the dose, the frequency of the dose, and/or the number of applications of the dose may be increased. Similarly, if, after a period of time has passed following the initial administration of the composition (for example, about 7 to 14 days), the androgen concentration in the blood serum of the patient is determined and found to be above the normal adult concentration thereof, the amount of the dose, the frequency of the dose, and/or the number of applications of the dose may be decreased.

In situations where a unit dose is applied, one or more of such unit doses may be administered to a patient, depending upon the condition to be treated, the amount of androgen to be delivered, and the frequency of administration. The number of such unit doses may be increased or decreased as needed, depending upon, as stated above, whether a desired clinical effect has been achieved and the concentration of androgen in the blood serum of the patient treated.

The composition of the present invention may be formulated by the use of conventional means, for example, by mixing and stirring the ingredients. Conventional equipment may be used. One of the advantages of the present invention is the ability to formulate the composition without resorting to unusual means to achieve the desired result. Simple glassware or stainless steel mixing vessels may be used. The composition can be formulated typically at room temperature or slightly above and at atmospheric pressures.

EXAMPLES

The following includes examples of compositions of the present invention and of comparative compositions.

Example 1

The example below describes the preparation of a composition which can be used as a topical gel for the delivery of testosterone and which is illustrative of a composition of the present invention. The concentrations of the ingredients comprising the composition are given in percent by weight relative to the total weight of the composition.

|  | Wt. % |
|---|---|
| testosterone, micronized, USP (B&B) | 1.0 |
| oxacyclohexadecan-2-one - enhancer | 8.0 |
| propylene glycol, USP - co-enhancer | 5.0 |
| carboxypolymethylene (B F Goodrich; sold as Carbopol 980 ®) - thickening agent | 1.5 |
| acrylic acid/alkyl methacrylate copolymer (B F Goodrich; sold as Pemulen-TR1) - thickening agent | 0.3 |
| ethanol, 200 proof, USP - solvent | 73.6 |
| glycerin, USP - co-solvent, emollient, humectant, and protein stabilizer | 5.0 |
| polyethylene glycol 1000, NF - crystallization inhibitor | 0.5 |
| tris amino crystal - neutralizing agent | 0.1 |
| water, sterile, for irrigation, USP | 5.0 |

A composition comprising the above ingredients was prepared in a lot size of 1000 grams. All ingredients were weighed accurately to two decimal points and then added to a vessel. Oxacyclohexadecan-2-one, ethanol, propylene glycol, and glycerin were weighed in a bottle beaker. All compounding steps took place at approximately 22° C. In between each step of addition and during stirring, a teflon stopper was placed on top of the vessel to prevent evaporation.

Eighty grams of oxacyclohexadecan-2-one in solid form were warmed in a 40 to 50° C. water bath until molten and added to a vessel. Four-hundred grams of ethanol were then added to the vessel white using portions to repeatedly rinse out the bottle beaker which contained oxacyclohexadecan-2-one. Fifty grams of propylene glycol and 50 grams of glycerin were then added separately, in that order, to the vessel and the resulting mixture was stirred gently using an electric stirrer until the solids were free to move. Ten grams of testosterone powder were then added to the vessel and the resulting mixture was stirred until the testosterone was dissolved completely. Five grams of polyethylene glycol were added thereafter to the vessel and the resulting mixture was stirred until the polyethylene glycol was dissolved completely. Three grams of acrylic acid/alkyl methacrylate copolymer and 15 grams of carboxypolymethylene were then added separately, in that order, to the vessel and the resulting mixture was then stirred for approximately one hour and twenty minutes. Three hundred and thirty-six grams of ethanol were then added to the vessel while using portions of the ethanol to repeatedly rinse out the bottle beakers previously used. While stirring the contents of the vessel, 50 grams of water and 1 gram of tris amino crystal were combined and weighed in one of the previously used bottle beakers, shaken until dissolved, and slowly added dropwise over 20 minutes to the center of the vessel, near the vortex, using a disposable polyethylene pipette. Stirring of the resulting mixture continued for approximately 18 hours. The above order or addition was not critical. There was recovered a colorless, clear to translucent gel with a viscosity of about 3,500 cps (as measured under standard conditions of measurement) and a musk-like fragrance. The gel is capable of being squeezed from a tube or a sachet and of being dispensed from a metered pump.

Example 2

The example below describes the preparation of a composition which can be used as a topical gel for the delivery of dihydrotestosterone (DHT) and which is illustrative of a composition of the present invention. The concentrations of the ingredients comprising the composition are given in percent by weight relative to the total weight of the composition.

|  | Wt. % |
|---|---|
| dihydrotestosterone (Diosynth) | 1.0 |
| oxacyclohexadecan-2-one - enhancer | 1.0 |
| propylene glycol, USP - co-enhancer | 5.0 |
| carboxypolymethylene (B F Goodrich; sold as Carbopol 980 ®) - thickening agent | 1.0 |
| acrylic acid/alkyl methacrylate copolymer (B F Goodrich; sold as Pemulen-TR1) - thickening agent | 0.5 |
| ethanol, 200 proof, USP - solvent | 74.0 |
| glycerin, USP - co-solvent, emollient, humectant, and protein stabilizer | 1.0 |
| polyethylene glycol 400, NF - crystallization inhibitor | 0.25 |
| tris amino crystal - neutralizing agent | 0.08 |
| water, sterile, for irrigation, USP | 16.17 |

A composition comprising the above ingredients was prepared in a lot size of 400 grams. All ingredients were weighed accurately to two decimal points and then added to a vessel. Oxacyclohexadecan-2-one, ethanol, propylene glycol, and glycerin were weighed in a bottle beaker. All compounding steps took place at ambient temperature In between each step of addition and during stirring, a teflon stopper was placed on top of the vessel to prevent evaporation.

Four grams of oxacyclohexadecan-2-one in solid form were added to a vessel. Ethanol was then added to the vessel while using portions to repeatedly rinse out the bottle beaker which contained oxacyclohexadecan-2-one. Twenty grams of propylene glycol and 4 grams of glycerin were then added separately, in that order, to the vessel and the resulting mixture was stirred gently using an electric stirrer until the solids were free to move. Four grams of DHT were then added to the vessel and the resulting mixture was stirred until the testosterone was dissolved completely. One gram of polyethylene glycol was added thereafter to the vessel and the resulting mixture was stirred until the polyethylene glycol was dissolved completely. Two grams of acrylic acid/alkyl methacrylate copolymer and 4 grams of carboxypolymethylene were then added separately, in that order, to the vessel and the resulting mixture was then stirred for approximately one hour and twenty minutes. The remainder of the ethanol (a total of 296 grams of ethanol was used in the making of this gel) was then added to the vessel while using portions of the ethanol to repeatedly rinse out the bottle beakers previously used. While stirring the contents of the vessel, 64.68 grams of water and 0.32 gram of tris amino crystal were combined and weighed in one of the previously used bottle beakers and shaken until dissolved. The above order or addition was not critical.

Example 3

The example below describes the preparation of a composition which can be used as a topical gel for the delivery of dihydrotestosterone (DHT) and which is illustrative of a composition of the present invention. The concentrations of the ingredients comprising the composition are given in percent by weight relative to the total weight of the composition. This composition is similar to that described in Example 2 except that slightly less ethanol and slightly greater amounts of glycerin, polyethylene glycol 400, and water were used.

| | Wt. % |
|---|---|
| dihydrotestosterone (Diosynth) | 1.0 |
| oxacyclohexadecan-2-one - enhancer | 1.0 |
| propylene glycol, USP - co-enhancer | 5.0 |
| carboxypolymethylene (B F Goodrich; sold as Carbopol 980 ®) - thickening agent | 1.0 |
| acrylic acid/alkyl methacrylate copolymer (B F Goodrich; sold as Pemulen-TR1) - thickening agent | 0.5 |
| ethanol, 200 proof, USP - solvent | 69.6 |
| glycerin, USP - co-solvent, emollient, humectant, and protein stabilizer | 5.0 |
| polyethylene glycol 400, NF - crystallization inhibitor | 0.5 |
| tris amino crystal - neutralizing agent | 0.08 |
| water, sterile, for irrigation, USP | 16.32 |

A composition comprising the above ingredients was prepared in a lot size of 400 grams. All ingredients were weighed accurately to two decimal points and then added to a vessel. Oxacyclohexadecan-2-one, ethanol, propylene glycol, and glycerin were weighed in a bottle beaker. All compounding steps took place at ambient temperature In between each step of addition and during stirring, a teflon stopper was placed on top of the vessel to prevent evaporation.

Four grams of oxacyclohexadecan-2-one in solid form were added to a vessel. Ethanol was then added to the vessel while using portions to repeatedly rinse out the bottle beaker which contained oxacyclohexadecan-2-one. Twenty grams of propylene glycol and 20 grams of glycerin were then added separately, in that order, to the vessel and the resulting mixture was stirred gently using an electric stirrer until the solids were free to move. Four grams of DHT were then added to the vessel and the resulting mixture was stirred until the testosterone was dissolved completely. Two grams of polyethylene glycol were added thereafter to the vessel and the resulting mixture was stirred until the polyethylene glycol was dissolved completely. Two grams of acrylic acid/alkyl methacrylate copolymer and 4 grams of carboxypolymethylene were then added separately, in that order, to the vessel and the resulting mixture was then stirred for approximately one hour and twenty minutes. The remainder of the ethanol (a total of 278.4 grams of ethanol was used in the making of this gel) was then added to the vessel while using portions of the ethanol to repeatedly rinse out the bottle beakers previously used. While stirring the contents of the vessel, 65-28 grams of water and 0.32 gram of tris amino crystal were combined and weighed in one of the previously used bottle beakers and shaken until dissolved. The above order or addition was not critical.

Comparative Example C-1

The following is the composition of AndroGel®, a topical 1% testosterone gel: testosterone USP (testosterone comprises 1 wt. % of this composition), isopropyl myristate, carboxyvinyl polymer, sodium hydroxide, purified water, and ethanol (ethanol comprises 67.0 wt. % of this composition).

The following is a description of the comparative use of the AndroGel® composition (hereafter "C-1 composition") and a composition of the present invention (hereafter "No. 1 composition"). The formulation of the No. 1 composition is as described in Example 1 with the exception that tromethamine, and not tris amino, was used as the neutralizing agent. Since large scale production was used to produce the No. 1 composition, various process and equipment changes were made as appropriate. Such appropriate changes are known to those of skill in the art and include changes in order of ingredient additions and mixing times. In addition, during the manufacturing process an overage of ethanol was added for the purpose of compensating for the evaporation thereof which occurs when larger equipment is used.

A total of 180 patients were screened for the present study. Twenty-nine hypogonadal male patients (25 Caucasian, 2 Asian, 1 Black, and 1 Hispanic) were selected for treatment. The mean age of these patients was 61.2 (±8.9) years, mean height was 70.2 (±2.7) inches, and mean body-mass index was 27.1 (±3.1). Nineteen patients had an 0800 h (±30 min) testosterone concentration in the blood serum of below 250 ng/dL. Ten patients had an 0900 h (±30 min) testosterone concentration in the blood serum of between 250 and 300 ng/dL. Except for male hypogonadism, the patients were in generally good health as evidenced by medical history, physical examination, clinical laboratory evaluations, and electrocardiogram obtained within 3 weeks prior to initial study drug administration. The study was conducted at the Orlando Clinical Research Center, Orlando, Fla. USA.

The present study was conducted as a randomized, open-label, two-way complete crossover study. The patients each received a single 5 g dose of the composition of the No. 1 composition and a single 5 g dose of the C-1 composition seven days apart at different body sites (right/left shoulder). The composition was applied by the patient, using his hands, to intact, clean, and dry shoulder skin and rubbed until dry. Each dose contained 50 mg testosterone. Approximately 10 mL of whole blood samples were collected prior to dosing and at 0.5, 1, 1.5, 2, 3, 4, 5, 6, 8, 10, 12, 15, 18, 24, and 48 hours after dosing. The patients were housed and supervised during each dosing period from approximately 12 hours prior to dosing until after the 24-hour blood collection was completed. The 48-hour blood collection was collected the following day.

Serum from the collected blood samples were separated by centrifugation of the blood samples at 1500×g for 10 minutes at 18° C. The resulting sera were transferred into plastic tubes and immediately frozen and stored at −20° C. (±3° C.) until assayed. The assay for total testosterone (T) was performed using the Coat-a-Count® Total Testosterone Assay Kit produced by Diagnostics Products Corporation. The assay for free testosterone (FT) was performed using the Coat-a-Count® Free Testosterone Assay Kit produced by Diagnostics Products Corporation. The assay for dihydrotestosterone (DHT) was performed using the Active™ Dihydrotestosterone Assay Kit produced by Diagnostics Systems Laboratories. All assays were performed by ICON Laboratories, New York, USA.

Serum concentrations of T, FT, and DHT were measured and the maximum concentrations thereof achieved over the 48-hour period ($C_{max}$) were determined. A serum concentration (not baseline-adjusted) vs. time curve was plotted for T, FT, and DHT (FIG. 1 shows the curve for T). The area under the serum concentration vs. time curve from 0 to 24 hours as determined using the linear trapezoidal rule ($AUC_{0-24}$) was measured for T, FT, and DHT. The baseline-adjusted results are summarized in Tables 1 to 3 below.

TABLE 1

Baseline Adjusted Total Testosterone - Mean (Standard Deviation) $C_{max}$ and $AUC_{0-24}$

| Composition | $C_{max}$ (ng/dL) | $AUC_{0-24}$ (ng · h/dL) |
|---|---|---|
| No. 1 | 480 (±70.3) | 5864.5 (±77.9) |
| C-1 | 368 (±60.9) | 4499.1 (±77.9) |

TABLE 2

Baseline Adjusted Free Testosterone - Mean (Standard Deviation) $C_{max}$ and $AUC_{0-24}$

| Composition | $C_{max}$ (ng/dL) | $AUC_{0-24}$ (ng · h/dL) |
|---|---|---|
| No. 1 | 20.08 (±77.8) | 240.7 (±75.4) |
| C-1 | 14.55 (±69.8) | 164.2 (±90.0) |

TABLE 3

Baseline Adjusted Dihydrotestosterone - Median (Range) $C_{max}$ and $AUC_{0-24}$**

| Composition | $C_{max}$ (pg/dL) | $AUC_{0-24}$ (pg · h/dL)* |
|---|---|---|
| No. 1 | 321 (23 to 964) | 4891.0 (257.5 to 15259.1) |
| C-1 | 313 (16 to 1038) | 4091.7 (225.0 to 16034.5) |

*One patient was excluded for $AUC_{0-24}$ because there was insufficient sample volume for analysis in the second period.
**Assumptions of normality were not satisfied for ANOVA model. Therefore, non-parametric analysis was performed.

The above values in Tables 1 to 3 were estimated using WinNonlin pharmacokinetic software. The $C_{max}$, and $AUC_{0-24}$ values above are baseline-adjusted, with baseline being the pre-dose concentration. The adjustment for $C_{max}$ was made by subtracting the pre-dose concentration from the measured concentration. Several negative values were generated. These values were imputed with zero unless observed at the last sampling time point, in which case they were ignored for pharmacokinetic purposes. The adjustment for $AUC_{0-24}$ was made by subtracting the pre-dose concentration of testosterone in the blood serum of the patient from the measured concentration thereof at each sampling time over the 24-hour period (it is assumed that, in hypogonadal patients, the concentration of testosterone over the 24-hour period does not vary greatly).

For T, the mean baseline-adjusted $C_{max}$ following administration of the No. 1 composition was approximately 30% greater than the mean baseline-adjusted 1 following administration of the C-1 composition. For FT, the mean baseline-adjusted $C_{max}$ following administration of the No. 1 composition was approximately 38% greater than the mean baseline-adjusted $C_{max}$ following administration of the C-1 composition. For DHT, the median baseline-adjusted $C_{max}$ following administration of the No. 1 composition was approximately 2.5% greater than the median baseline-adjusted $C_{max}$ following administration of the C-1 composition.

For T, the mean $AUC_{0-24}$ following administration of the No. 1 composition was approximately 30% greater than the mean $AUC_{0-24}$ following administration of the C-1 composition. For FT, the mean $AUC_{0-24}$ following administration of the No. 1 composition was approximately 45% greater than the mean $AUC_{0-24}$ following administration of the C-1 composition. For DHT, the mean $AUC_{0-24}$ following administration of the No. 1 composition was approximately 20% greater than the mean $AUC_{0-24}$ following administration of the C-1 composition.

As can be seen from FIG. 1, normal male adult total testosterone (T) concentrations (300 ng/dL to 100 ng/dL) were sustained over a period of time following the administration of one 5 gram dose of the No. 1 composition.

In the use of the No. 1 and C-1 compositions, three concentration maxima were observed during the 48-hour post-application period. These maxima occurred at approximately 3- to 4-hours post-application, 8- to 10-hours post-application, and 18- to 24-hours post application (see FIG. 1).

Comparative Example C-2

The following is the composition which is used in the Androderm® patch, a transdermal patch used for delivering testosterone: testosterone USP; alcohol USP; glycerine USP; glycerol monooleate; methyl laurate; purified water USP; and acrylic acid copolymer.

The Androderm® patch has six components. Proceeding from the exterior toward the surface attached to the skin, the system is composed of; (A) a layer of metallized polyester/Surlyn® (an ethylene-methacrylic acid copolymer/ethylene vinyl acetate backing film with alcohol resistant ink); (B) a reservoir containing the above composition; (C) a permeable polyethylene microporous membrane; and (D) a peripheral layer of acrylic adhesive surrounding the central active drug delivery area of the system. Prior to opening of the system and application to the skin, the central delivery surface of the system was sealed with a peelable laminate disc composed of a five-layer laminate containing polyester, polyesterurethane adhesive, aluminum foil, polyesterurethane adhesive, and polyethylene. The disc was attached to and removed with a release liner, a silicone-coated polyester film, which was removed before the system was used.

The following is a description of the comparative use of the compositions of Example 1 (the "No. 1 composition") and of Example C-2 (hereafter the "C-2 composition").

Four hundred six male patients between 20 and 80 years of age were treated at 43 centers in the United States. The patients were hypogonadal and exhibited morning total testosterone (T) concentrations at screening of less than or equal to 10.4 nmol/L (as measured at a central laboratory) and one or more symptoms of low testosterone (e.g., fatigue, decreased muscle mass, reduced libido, and reduced sexual functioning). Except for male hypogonadism, the patients were in generally good health. Patients were excluded from the study if they had any generalized skin irritation or disease that might have interfered with androgen absorption, had received any estrogen therapy, a luteinizing hormone-releasing hormone antagonist, or human growth hormone therapy, or had a history of drug abuse within 12 months. Also excluded were patients who had used either Viagra® within 30 days, or were treated with testosterone or anabolic supplements within 6 weeks prior to the study. The characteristics of the patients, as divided by test group (described below), are summarized in Table 4 below. Compositions identified in Table 4 as "No. 1", "C-2", and "placebo" were administered to the patients in the test groups as explained in the discussion which follows Table 4.

TABLE 4

Patient Characteristics

| | No. 1 Groups | | C-2 Group | Placebo Group | Total |
|---|---|---|---|---|---|
| | 5 g/day | 10 g/day | | | |
| Demographics | | | | | |
| No. of patients | 99 | 106 | 102 | 99 | 406 |
| Age (yrs) | 58.1 ± 9.7 | 56.8 ± 10.6 | 60.5 ± 9.7 | 56.8 ± 10.8 | 58.0 ± 103 |
| Height (cm) | 178 ± 6 | 178 ± 8 | 178 ± 6 | 180 ± 7 | 179 ± 7 |
| Weight (kg) | 95.7 ± 13.4 | 95.7 ± 14.4 | 95.1 ± 13.5 | 98.5 ± 15.6 | 96.2 ± 14.2 |
| BMI* | 30.0 ± 3.7 | 29.9 ± 3.3 | 29.9 ± 3.8 | 30.3 ± 3.8 | 30.0 ± 3.6 |
| Testosterone (nmol/L)† | 8.1 ± 2.0 | 8.1 ± 2.2 | 8.3 ± 2.4 | 7.9 ± 2.8 | 8.1 ± 2.3 |
| Cause of Male Hypogonadism | | | | | |
| Primary (n) | 8 | 7 | 4 | 3 | 22 |
| Secondary (n) | 91 | 98 | 98 | 95 | 382 |
| Aging (%) | 70.7 | 58.1 | 66.7 | 61.2 | 64.1 |
| Normogonadotrophic (%) | 19.2 | 30.5 | 26.5 | 31.6 | 27.0 |

Demographic values are expressed as means ± one standard deviation
n = number of patients
*BMI = body mass index
†Testosterone = 8 a.m. serum concentration at screening exam One hundred-and-six patients received 10 g/day of the No. 1 composition contained in two 5 g/day tubes (hereafter the "10 g/day No. 1 group"); 99 patients received 5 g/day of the No. 1 composition, contained in one 5 g/day tube, and 5 g/day of a placebo gel, contained in another 5 g/day tube (hereafter the "5 g/day No. 1 group"); 102 patients were treated using two Androderm® patches a day, each patch containing the C-2 composition with 12.2 mg testosterone and each delivering approximately 2.5 mg/day testosterone for a total dosage of approximately 5.0 mg/day testosterone (hereafter the "C-2 group"); and 99 patients received 10 g/day of the above placebo gel contained in two 5 g/day tubes (hereafter the "placebo group"). The placebo gel was modeled after the gel of the No. 1 composition with the exception that testosterone is not present and additional ethanol was added. The study was double-blinded for the No. 1 groups and the placebo group and open-label for the C-2 group.

All study drug treatments were applied in the morning and repeat applications occurred at the same time of day for the duration of the study. Each of the patients in the No. 1 groups and the placebo group applied the contents of two tubes a day with the contents of one tube applied to the skin of one shoulder and the contents of the other tube applied to the skin of the other shoulder. Patients allocated to receive the C-2 composition-containing patches applied two adhesive patches daily. Application sites included intact and clean skin of the back, abdomen, upper arms, and thighs. Patches were to be worn for 24 hours and then replaced each morning at approximately the same time.

Forty-four percent of the patients assigned originally to apply 5 g/day of the No. 1 composition had a mean total testosterone concentration ($C_{avg}$) on Day 30 of less than 10.4 nmol/L (300 ng/dL) and were thus titrated on Day 60 to a dose of 10 g/day of said composition. Four percent of the patients assigned originally to apply 10 g/day of the No. 1 composition had a $C_{avg}$ on Day 30 of greater than 34.7 nmol/L (1,000 ng/dL) and were thus titrated on Day 60 to a dose of 5 g/day of said composition.

Ninety percent of the patients in the No. 1 groups, 92% of the patients of the placebo group, and 75% of the patients in the C-2 group completed the 90-day study. The primary reason for the higher rate of discontinuations in the C-2 group was adverse events (17%), with the majority of events being related to skin irritations at the patch site. Study protocol compliance was 94.9% for the placebo group, 95.5% for the C-2 group, and 97.1% for the No. 1 group. Ninety-three percent of patients had a compliance of 80% or greater.

A baseline 24-hour profile for total testosterone (T), free testosterone (FT), and dihydrotestosterone (DHT) concentrations in the blood serum was measured for the patients using serum samples taken over a 24-hour period at 0, 2, 4, 8, 12, and 24 hours on the day immediately prior to the day of the first dose of the study drug. On Days 30 and 90, the patients had a 24-hour profile for T, FT, and DHT concentrations in the blood serum measured using data collected from serum samples taken pre-dose and at 2, 4, 8, 12, and 24-hours after drug administration. The mean total testosterone concentration over the 24-hour period ($C_{avg}$), the minimum testosterone concentration during the 24-hour period ($C_{min}$), and the maximum testosterone concentration during the 24 hour period ($C_{max}$) were measured. The results are summarized in Tables 5 and 6.

The assay for T was performed using the Coat-a-Count® Total Testosterone Assay Kit produced by Diagnostics Products Corporation. The assay for FT was performed using the Coat-a-Count® Free Testosterone Assay Kit produced by Diagnostics Products Corporation. The assay for DHT was performed using the Active™ Dihydrotestosterone Assay Kit produced by Diagnostics Systems Laboratories.

Table 5 below shows total testosterone (T) concentrations for the above groups measured prior to treatment (baseline) and at Days 30 and 90.

TABLE 5

Testosterone Pharmacokinetics
Testosterone (nmol/L): Mean Days 30 and 90

| | | No. 1 Groups | | | |
|---|---|---|---|---|---|
| | | 5 g/day | 10 g/day | C-2 Group | Placebo Group |
| | | Day 30 | | | |
| $C_{avg}$ | baseline | 8.6 ± 2.8 | 7.8 ± 2.8 | 8.2 ± 2.8 | 7.5 ± 2.8 |
| | actual | 12.7 ± 6.5 | 21.3 ± 9.9*** | 12.7 ± 4.2 | 7.5 ± 2.8 |
| $C_{min}$ | baseline | 6.8 ± 2.4 | 6.2 ± 2.6 | 6.7 ± 2.3 | 5.9 ± 2.3 |
| | actual | 7.7 ± 4.4* | 13.6 ± 6.5*** | 6.2 ± 2.9 | 5.7 ± 2.2 |
| $C_{max}$ | baseline | 10.7 ± 3.6 | 9.9 ± 3.2 | 10.2 ± 3.7 | 9.5 ± 3.6 |
| | actual | 18.8 ± 12.9* | 31.2 ± 19.8*** | 18.8 ± 6.9 | 9.4 ± 3.8 |
| | | Day 90 | | | |
| $C_{avg}$ | baseline | 9.2 ± 3.4 | 7.7 ± 2.4 | 8.3 ± 2.8 | 7.6 ± 2.8 |
| | actual | 13.8 ± 8.1 | 17.1 ± 8.2*** | 11.9 ± 4.6 | 7.3 ± 2.7 |
| $C_{min}$ | baseline | 7.4 ± 2.8 | 6.1 ± 2.3 | 6.7 ± 2.1 | 6.0 ± 2.4 |
| | actual | 8.7 ± 3.9*** | 10.9 ± 6.0*** | 5.7 ± 2.8 | 5.9 ± 2.4 |
| $C_{max}$ | baseline | 11.3 ± 4.1 | 9.8 ± 2.9 | 10.3 ± 3.7 | 9.5 ± 3.6 |
| | actual | 19.5 ± 12.2 | 24.4 ± 13.8*** | 18.5 ± 8.2 | 9.1 ± 3.5 |

Values are expressed as means ± one standard deviation
Change from baseline significant versus C-2 group
*p < 0.05,
***p < 0.001

For total testosterone (T), at baseline mean $C_{avg}$ for all groups were below the normal adult male range (10.4 to 34.7 nmol/L). By Day 30, the mean $C_{avg}$ for the 5 g/day No. 1 group had increased about 50% over baseline with a similar increase being evidenced in the C-2 group and the mean $C_{avg}$ for the 10 g/day No. 1 group had increased about 173% over baseline (a significant difference (P<0.001) as compared to the C-2 group). $C_{avg}$ for the placebo group did not change. The degree of fluctuation during a day in total testosterone values ($[C_{max}-C_{min}]/C_{avg}$) was significantly smaller in the two No. 1 groups as compared to the C-2 group. The mean C, was significantly increased in both the No. 1 groups while $C_{min}$ for the C-2 group declined. By Day 90, similar results were seen across the treatment groups. Approximately 75% of the patients in the 5 g/day No. 1 group and 80% of the patients in the 10 g/day No. 1 group had $C_{avg}$ values above 10.4 nmol/L. By contrast, 57% of the patients in the C-2 group and 10% of the patient in the placebo group had $C_{avg}$ values above 10.4 mmol/L. The mean $C_{min}$ were significantly increased in both the No. 1 groups while $C_{min}$ declined in the C-2 group.

Table 6 below shows serum dihydrotestosterone concentrations for the above groups measured prior to treatment (baseline) and at Days 30 and 90.

TABLE 6

Dihydrotestosterone Pharmacokinetics
Dihydrotestosterone (nmol/L): Mean Days 30 and 90

| | | No. 1 Groups | | | |
|---|---|---|---|---|---|
| | | 5 g/day | 10 g/day | C-2 Group | Placebo Group |
| | | Day 30 | | | |
| $C_{avg}$ | baseline | 0.4 ± 0.2 | 0.4 ± 0.2 | 0.4 ± 0.2 | 0.3 ± 0.2 |
| | actual | 1.2 ± 0.7*** | 1.9 ± 1.0*** | 0.6 ± 0.3 | 0.4 ± 0.2 |
| $C_{min}$ | baseline | 0.3 ± 0.1 | 0.3 ± 0.1 | 0.3 ± 0.1 | 0.2 ± 0.1 |
| | actual | 0.8 ± 0.6*** | 1.4 ± 0.9*** | 0.4 ± 0.2 | 0.3 ± 0.2 |
| $C_{max}$ | baseline | 0.5 ± 0.2 | 0.5 ± 0.3 | 0.5 ± 0.3 | 0.5 ± 0.2 |
| | actual | 1.7 ± 1.0*** | 2.6 ± 1.4*** | 0.8 ± 0.7 | 0.5 ± 0.3 |
| | | Day 90 | | | |
| $C_{avg}$ | baseline | 0.5 ± 0.2 | 0.4 ± 0.2 | 0.4 ± 0.2 | 0.4 ± 0.2 |
| | actual | 1.5 ± 0.7*** | 1.8 ± 0.9*** | 0.6 ± 0.3 | 0.4 ± 0.2 |
| $C_{min}$ | baseline | 0.3 ± 0.1 | 0.2 ± 0.1 | 0.3 ± 0.1 | 0.3 ± 0.1 |
| | actual | 1.0 ± 0.6*** | 1.2 ± 0.7*** | 0.3 ± 0.2 | 0.3 ± 0.2 |
| $C_{max}$ | baseline | 0.6 ± 0.2 | 0.5 ± 0.2 | 0.5 ± 0.2 | 0.5 ± 0.2 |
| | actual | 2.0 ± 0.9*** | 2.3 ± 1.2*** | 0.8 ± 0.4 | 0.5 ± 0.3 |

Values are expressed as means ± one standard deviation
Change from baseline significant versus C-2 group
***p < 0.001

For DHT, at baseline mean $C_{avg}$ for all groups were below the normal adult male range (0.9 to 2.6 nmol/L). Mean changes in $C_{avg}$ from baseline to Day 30 for the 5 g/day and 10 g/day No. 1 groups were over four- and seven-fold greater, respectively, than changes observed in the C-2 treatment group (P<0.001 for each comparison). In addition, $C_{min}$ in both of the No. 1 groups was increased to a significantly greater degree than $C_{min}$ in the C-2 group (P<0.001 for each comparison).

Total body mass (TBM), lean body mass (LBM), fat mass (FM) and percentage fat (% F) were measured for the above patients using dual energy x-ray absorptiometry (DXA) on the day immediately prior to the day of the first dose of the study drug and on Day 90 (the results are shown in FIG. 2). The measurements were centrally monitored and analyzed by Synarc, Inc. (Maynard, Mass., U.S.A.). At Day 90, LBM in the 10 g/day No. 1 group increased to a significantly greater degree than in the C-2 or the placebo group (P<0.05 for each comparison) with mean changes from baseline of 1.5±4.5, 1.7±2.6, 0.9±1.8, and 0.6±1.8 kg for the 5 g/day No. 1 group, 10 g/day No. 1 group, C-2 group, and placebo group, respectively. With the exception of the placebo group, all groups exhibited decreases in FM which were significant as compared to placebo (P<0.01). Reductions of 0.8±2.4, 0.8±2.0, 0.4±1.8, and 0.1±1.5 kg were noted in the 5 g/day No. 1 group, 10 g/day No. 1 group, C-2 group, and placebo group, respectively.

The incidence of treatment-related adverse events was 29.1%, 36.9%, 62.7%, and 40.4% in the 5 g/day No. 1 group, 10 g/day No. 1 group, C-2 group, and placebo group, respectively. While treatment in the No. 1 groups and the placebo group was relatively well tolerated over the 90-day study period, the C-2 group patients experienced a substantially higher rate of adverse events. Those most commonly seen were application-site erythema, application-site rash, application-site pruritus, application-site reactions, and application-site irritation.

No patients in the No. 1 groups discontinued due to skin reaction; whereas, 15% of patients discontinued in the C-2 group as a result of local dermal site reactions.

FIG. 3 provides a graphic illustration of the frequency distribution of patients having positive skin irritation scores. The scoring system was based on a five-point categorical series from 0 (no erythema) through 4 (intense erythema with edema and blistering/erosion). As can be seen, events occurred predominately in the C-2 group and only a few mild reactions occurred in the No. 1 and placebo groups. Additionally, the figure illustrates that the C-2-containing patches acted as an irritant in some patients who experienced classic signs of contact dermatitis and that the No. 1 group did not experience any more skin irritation than the placebo group.

The invention claimed is:

1. A method for maintaining a therapeutically effective concentration of testosterone in the blood serum of a male for treating hypogonadism which comprises transdermally delivering to the male by applying to the skin a composition which is in the form of a topical gel, which has a viscosity of about 2000 to about 6000 cps and a pH of about 4 to about 8, and comprises: (A) about 0.1 to about 5 wt. % of testosterone; (B) about 0.5 to about 25 wt. % of a macrocyclic enhancer selected from the group consisting of 3-methylcyclopentadecanone, 9-cycloheptadecen-1-one, cyclohexadecanone, cyclopentadecanone, oxacyclohexadecan-2-one and mixtures thereof (C) about 1 to about 6 wt. % of a thickening agent; (D) a mixture of solvents which include: (i) about 60 to about 75 wt. % of ethanol or isopropanol; and (ii) propylene glycol and glycerin as co-solvents.

2. The method of claim 1 further comprising about 0.001 to about 5 wt. % of polyethylene glycol as a crystallization inhibitor.

3. The method of claim 1 wherein said composition is maintained on said skin for a period of time sufficient for delivery of the testosterone to the body of the male and is applied to the skin in the form of a unit dose which contains about 1 to about 300 mg of testosterone and such that, following a single application of the unit dose to the skin, the amount of circulating testosterone ($AUC_{0-24}$) in the blood serum of the male achieved in the 24-hour period following the application is about 100 to about 35,000 ng·h/dL greater than the amount of circulating testosterone ($AUC_{0-24}$) in the blood serum of the male than would have been achieved in the same 24-hour period had the dose not been administered.

4. The method of claim 1 wherein the macrocyclic enhancer is 3-methylcyclopentadecanone.

5. The method of claim 1 wherein the macrocyclic enhancer is 9-cycloheptadecen-1-one.

6. The method of claim 1 wherein the macrocyclic enhancer is cyclohexadecanone.

7. The method of claim 1 wherein the macrocyclic enhancer is cyclopentadecanone.

8. The method of claim 1 wherein the macrocyclic enhancer is oxacyclohexadecan-2-one.

* * * * *